United States Patent
Liu (10) Patent No.: US 9,885,013 B2
(45) Date of Patent: Feb. 6, 2018

(54) DEVICE FOR SEPARATING CELLS IN FLUID

(71) Applicant: The Hunan Cycle Filter Medical Technology Co., Ltd., Changsha, Hunan (CN)

(72) Inventor: Tao Liu, Hunan (CN)

(73) Assignee: The Hunan Cycle Filter Medical Technology Co., Ltd., Hunan (CN)

( * ) Notice: Subject to any disclaimer, the term of this patent is extended or adjusted under 35 U.S.C. 154(b) by 47 days.

(21) Appl. No.: 15/111,279

(22) PCT Filed: Jan. 14, 2015

(86) PCT No.: PCT/CN2015/070652
§ 371 (c)(1),
(2) Date: Jul. 13, 2016

(87) PCT Pub. No.: WO2016/112501
PCT Pub. Date: Jul. 21, 2016

(65) Prior Publication Data
US 2017/0002308 A1    Jan. 5, 2017

(30) Foreign Application Priority Data

Jan. 14, 2014  (CN) .......................... 2014 1 0016566

(51) Int. Cl.
*A61M 1/36*         (2006.01)
*B01D 63/06*        (2006.01)
(Continued)

(52) U.S. Cl.
CPC .......... *C12M 47/04* (2013.01); *A61M 1/3633* (2013.01); *B01D 63/062* (2013.01);
(Continued)

(58) Field of Classification Search
None
See application file for complete search history.

(56) References Cited

U.S. PATENT DOCUMENTS 7,022,518 B1 *  4/2006  Feye ...................... C12M 23/08
                                                    435/297.1
7,424,821 B1 *  9/2008  Benjamin .............. B01D 65/10
                                                    73/73
(Continued)

FOREIGN PATENT DOCUMENTS

CN         201046965 Y      4/2008

OTHER PUBLICATIONS

Cui, et al., "Preparation of Polycarbonate Nuclear Track Microfilters and Their Applications," Nuclear Techniques, vol. 1 (1982) [with English translation of Abstract].

*Primary Examiner* — Krishnan S Menon
(74) *Attorney, Agent, or Firm* — Fish & Richardson P.C.

(57) ABSTRACT

The present disclosure provides a device for separating cells in fluid, comprising a first driving pump, a separation column, a detection column, a second driving pump, and several three-way valves and secondary driving pumps; one end of the separation column is connected with the first driving pump through a first three-way valve; the other end is connected with the second driving pump through a second three-way valve; the separation column includes at least five sub filtration columns in parallel; the sub filtration column comprises a fixing bracket and a track-etched membrane of polycarbonate or polyester material attached to the bottom of and the side surfaces all around the fixing bracket, wherein the pore diameter of the track-etched membrane is 5-25 μm. The device of the present disclosure not only provides a new method for accurately determining whether there are circulating tumor cells in the blood of the living animal and provides a new method for sorting and counting
(Continued)

the circulating tumor cells in the blood of the living animal, but also provides a pioneering new method and new device for therapy of the tumor transfer and removal of the tumor cells inside the body, and has extremely high economic and social values.

11 Claims, 8 Drawing Sheets

(51) Int. Cl.
| | |
|---|---|
| *C12M 1/00* | (2006.01) |
| *B01D 67/00* | (2006.01) |
| *C12M 1/12* | (2006.01) |
| *C12M 1/34* | (2006.01) |

(52) U.S. Cl.
CPC ........... *B01D 67/0032* (2013.01); *C12M 1/12* (2013.01); *C12M 25/06* (2013.01); *C12M 29/00* (2013.01); *C12M 41/40* (2013.01)

(56) References Cited

U.S. PATENT DOCUMENTS

2016/0243502 A1* 8/2016 Vincent .................. B01D 63/06
2017/0274134 A1* 9/2017 Min .................... A61M 1/0236

* cited by examiner

DEVICE FOR SEPARATING CELLS IN FLUID

TECHNICAL FIELD

The present disclosure relates to a technical field of separating cells in fluid, and specifically relates to a device for filtering and separating target cells in cell suspension by membranes.

BACKGROUND ART

In prior arts, when it is necessary to separate and detect circulating tumor cells (CTC) in the blood of a living animal (including a human body), cell sorting and counting are performed by drawing a certain volume of blood and then using a method such as the density gradient centrifugation. The density gradient centrifugation method uses a certain medium to form a continuous or discontinuous density gradient in a centrifugal tube, places the cell suspension or homogenate on top of the medium, and sorts the cells through gravity or centrifugal force field effects. Its disadvantages are as below: 1. due to the limitation of the centrifuge, it is impossible to simultaneously perform centrifugation on a large volume of the cell suspension and thereby separate the cells, and the efficiency is low; 2. the added medium may affect the cell activity and the property of the solution, and operations of removing the medium are time-consuming and labored; 3. the operation is complicated and has a high requirement on the medium configuration. Hence, a new device and method for separating and detecting the number of the circulating tumor cells in the blood of a living animal is needed in this field. In recent years, a method of separating the circulating tumor cells in the blood by using a track-etched membrane appears in this field. For example, "Preparation of polycarbonate nuclear track microfilters and their applications" by Huanhua CUI, Shicheng WANG, et al. discloses using a track microporous filter membrane to diagnose the circulating tumor cells in the blood, specifically, putting the circulating tumor cells retained on the track microporous filter membrane to be observed under a microscope. The inventor of the present disclosure also uses this membrane to separate the circulating tumor cells in the blood of some living animals (for example, rabbits), and diagnoses and counts the circulating tumor cells. However, a device corresponding to this method may only be able to separate the circulating tumor cells in very small portion of blood of the living animal at a time, and cannot effectively separate the circulating tumor cells in most or all of the blood of the living animal. In particular, for a larger living animal (for example, a human body), such defect is particularly significant. The reason is that, in order to maintain the living animal in a normal living state, it is impossible to evacuate all the blood from the living animal to separate the circulating tumor cells; otherwise the individual will die. In addition, because the number of the circulating tumor cells (CTC) in the blood is extremely small, the sensitivity of the separation and detection may be greatly reduced (the detection result may be incorrect easily) if only a small volume of the blood of the living animal is drawn to perform the separation and detection; but increase of the volume of the blood for processing may threaten the healthy and life of the living animal. Therefore, it is further necessary to provide a new device and method for separating and detecting the circulating tumor cells in a living animal (including a human body) in this field.

SUMMARY

The present disclosure solves the above technical problem with a brand-new idea. The inventor of the present disclosure achieves the above technical purpose by using a device combining "a separation column having a track-etched membrane" and "a main circulation conduit". A sample injection port 20 and a sample discharge port 21 of the device of the present disclosure are coupled to the two ends of a cell liquid container (arteries and veins of the living animal). The circular filtration and separation of the circulating tumor cells are achieved by the blood flowing circularly within the main circulation conduit of the device. Thus, accurate detection with high sensitivity of whether the blood of the living animal already contains the circulating tumor cells and accurate counting of all the circulating tumor cells in the blood of the living animal may be then conveniently achieved by collecting the circulating tumor cells. The use of the device of the present disclosure further brings two additional technical effects. One is that all the blood flowing through the device may circulate back into the body of the living animal, and no blood of the living animal will be wasted. The other one is that after the living animal whose blood contains circulating tumor cells uses the circulation device of the present disclosure, almost all the circulating tumor cells in the blood may be filtered out, so that the transfer of the circulating tumor cells from a primary lesion to other organs inside the body may be cut off. Thus, the device of the present disclosure has very significant economic interest and social interest.

The present disclosure provides a device for separating cells in fluid, which comprises a first driving pump communicating with an sample injection port, a separation column, a detection column, a second driving pump for driving cells separated from the separation column to enter the detection column, and several three-way valves as well as secondary driving pumps, wherein, one end of the separation column is connected with the first driving pump through a first three-way valve; the other end is connected with the second driving pump through a second three-way valve; the detection column is connected with a third channel port of the first three-way valve, and a third channel port of the second three-way valve is connected with a sample discharge port; wherein, a cell liquid container is detachably communicated between the sample injection port and the sample discharge port, so that the cell liquid container together with the device of the present disclosure forms a circulation passage; wherein, the device further comprises a main circulation conduit sequentially communicating with the sample injection port, the first driving pump, the first three-way valve, the separation column, the sample discharge port, the cell liquid container, and the sample injection port; wherein, a third three-way valve for adding anticoagulant physiological saline into the main circulation conduit is connected on the main circulation conduit, and is positioned between the sample injection port and the separation column; a fourth three-way valve for adding anticoagulant antagonist into the main circulation conduit is connected on the main circulation conduit, and is positioned between the sample discharge port and the separation column; the separation column includes at least five sub filtration columns in parallel; the sub filtration column comprises a fixing bracket and a track-etched membrane of polycarbonate or polyester material attached to the bottom of and the side surfaces all around the fixing brackets, the pore diameter of the track-etched membrane being 5-25 μm; wherein, the detection column comprises two portions which are movably connected, the outer sides of the free ends of said two portions are both provided with liquid channel ports adapted to the conduit, a sealed hollow cavity is formed between said two portions, and the hollow cavity is provided with one or more layers of the track-etched membranes of polycarbonate or polyester material, the pore diameter of the track-etched membrane being 5-25 μm.

The pore diameter of the track-etched membrane 7 provided by the present disclosure matches with the size of the circulating tumor cells to be separated, so that normal red blood cells, white blood cells and blood platelets as well as other small molecules in the blood may all pass through, while the circulating tumor cells are retained at the upstream side of the track-etched membrane 7.

The device of the present disclosure provides not only a new method for accurately determining whether there are circulating tumor cells in the blood of the living animal but also a new method for sorting and counting the circulating tumor cells in the blood of the living animal, and it further provides a pioneering new method and device for therapy of the tumor transfer and removal of the tumor cells inside the body, and has extremely high economic and social values.

In the present disclosure, the "anticoagulant physiological saline" means the physiological saline containing anticoagulants, wherein the anticoagulants are for example EDTA salt or citric acid salt, and the "anticoagulant physiological saline" is added into the main circulation conduit so that the fluid (blood containing circulating tumor cells) will not result in blood coagulation during the process of contacting the track-etched membrane 7 after entering the separation column 3. The "anticoagulant antagonist" means the physiological saline containing antagonist of anticoagulant, wherein the "antagonist of anticoagulant" is calcium salt, for example, calcium chloride. Before the blood in which the circulating tumor cells are filtered out is returned back into the body of the living animal (including a human body), it is necessary to add the "anticoagulant antagonist" into the main circulation conduit downstream of the separation column 3, so that the blood into which the anticoagulant is added will not poison the living animal due to the direct introduction of the blood into the living animal.

In the present disclosure, the track-etched membrane 7 may be provided on the outer side, inner side of the fixing brackets, or embedded in the brackets, and there is no limitation on this in the present disclosure. In the present disclosure, both of the separation column 3 and detection column 4 may be arranged freely either horizontally or vertically or in other manners, and the implementation of the present disclosure will not be affected. In the present disclosure, the detection column 4 functions to enrich the target cells so as to facilitate the observation and detection. The membrane in the detection column may be taken out and placed under the detection device to be detected (for example, to be observed and determined under the microscope or to count the target cells after dyeing). Thus, a more accurate definition of the detection column 4 should be a cell enrichment column. In the present disclosure, the track-etched membrane 7 in the separation column 3 requited to be a single-layer membrane, and stacking of two layers of the membranes is not allowed. The technical solution in which the inner side and outer side of the fixing bracket are provided with one layer of the track-etched membrane 7 respectively is not a preferable technical solution, because it will affect the flowing of the fluid in the main circulation conduit. The track-etched membrane 7 in the detection column 4 is also preferably a single-layer membrane; otherwise, the flowing velocity of the fluid may be greatly affected. However, the detection column 4 may be provided with two or more layers of the track-etched membranes 7 in total while a certain pitch is kept between the membranes. More preferably, there is only one layer of the track-etched membrane 7 in the detection column 4, while two or more detection columns 4 connected in series are preferably used for enriching the target cells, resulting in a theoretically more accurate number of the target cells.

In a specific embodiment, a first secondary pump is connected to a third channel port of the third three-way valve, and a second secondary pump is connected to a third channel port of the forth three-way valve.

In a specific embodiment, the third three-way valve is positioned between the sample injection port and the first driving pump, or the third three-way valve is positioned between the first driving pump and the separation column; the forth three-way valve is positioned between the sample discharge port and the second three-way valve, or the forth three-way valve is positioned between the second three-way valve and the separation column.

Preferably, the pore diameter of the track-etched membrane in the detection column is smaller than or equal to the pore diameter of the track-etched membrane in the separation column.

In a specific embodiment, the separation column comprises a liquid dispersion region positioned at one end close to the sample injection port and sub filtration columns positioned in a mid-section thereof. Preferably, one end surface of the liquid dispersion region is a port cover plate with a liquid channel port opened thereon, and the other end surface of the liquid dispersion region is a support plate with through holes corresponding to a total number of end surfaces of the sub filtration columns opened therein. Please see FIG. 3 for the configuration of the shown preferable technical solution. Furthermore, although the sub filtration columns 19 shown in FIG. 5 of the present disclosure are all in an elongated cylindrical shape, the sub filtration columns 19 are not limited to the elongated cylindrical shape, and may be in other shapes, such as an elongated strip shape with a triangle, rectangular cross-section, or a long sheet shape with an elongated rectangular cross-section.

In a specific embodiment, the driving pump is a peristaltic pump. Selecting the peristaltic pump as the driving pump may cause the flowing of the fluid to be more stable. Preferably, the first secondary pump or the second secondary pump is a peristaltic pump or a push-type infusion pump.

Preferably, the device according to the present disclosure further comprises a pressure sensor which is provided on the main circulation conduit and is positioned between the first driving pump and the separation column; and the device further comprises a conduit line heater.

Preferably, the pore diameters of the track-etched membranes in the separation column and the detection column are both 8-10 μm.

In a specific embodiment, the detection column is made of plasticized polyvinyl chloride.

Figure 8:
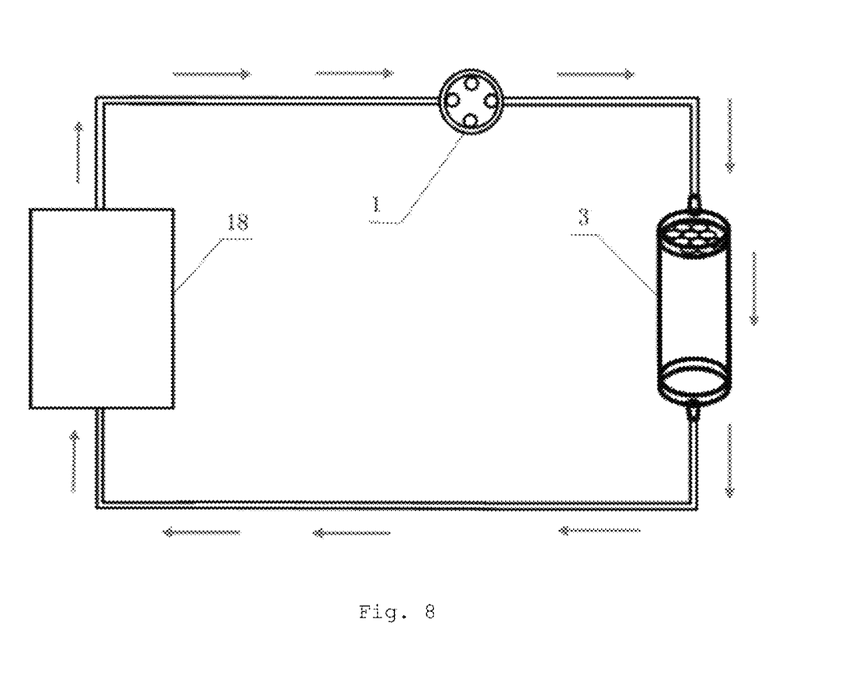
FIG. 8 is a schematic drawing showing the main circulation structure of the preferable embodiment of the present disclosure.

The present disclosure obtains the device by combining the "separation column having three-dimensional track-etched membrane" with the "circulating membrane separation structure", which has the following beneficial effects:

1. Separation of cells in the blood of the living animal: as seen from FIG. 8, the present disclosure performs filtration in a circulation manner, i.e., after the filtration of the liquid entered from an inlet of the system is completed, the liquid returns back into the original solution from an outlet of the system, and thus a circulation loop is formed. During a uninterrupted circulation process, particular cells with large volumes in the cell suspension are retained, while cells with small volumes pass through the filter membrane and return back into the solution. The advantage is that the total volume of the cell suspension outside the system (device) remains unchanged, wherein the number of the cells with small volumes remains unchanged.

Thus, the sample injection port of the device is connected with the artery of an animal, the sample discharge port of the device is connected with the vein of the animal. With the help of a power pump, the blood sample may be led out from the artery, and after the target cells of interest are separated through the membranes having a proper pore diameter on the separation column, other components are transfused back through the vein. In this way, it is possible to process as many blood samples as possible and separate more cells of interest while the survival of the animal is guaranteed (which further needs the help of adding the anticoagulant into the upstream end of the separation column in the main circulation conduit and adding the antagonist of the anticoagulant into the downstream end of the separation column). Compared with the traditional methods, the separation efficiency and separation sensitivity are significantly improved while the survival of the animal is guaranteed. In this way, multiple cell separations at multiple time points may be performed on the same animal. None of the current cell sorting methods may achieve the above effect.

2. Improvement of the separation efficiency: take a C-ISET separation column having a diameter of 6 centimeters and a length of 11 centimeters as an example, wherein 11 cylindrical sub filtration columns in parallel each of which has a diameter of 1 centimeter and a length of 10 centimeters may be placed in the C-ISET separation column. The separation column with this specification has an effective filtration area of 354 square centimeters, while the conventional filtration device (a disc-shaped separation column having one layer of the track-etched membrane, wherein the track-etched membrane is round-shaped, and the shape of which is similar to the structure of the detection column 4 in the present disclosure) with a diameter of 6 centimeters has an effective filtration area of merely 28.26 square centimeters. The separation column of the present disclosure has an effective filtration area that is 1252% of that of the traditional filtration device, which is 11.52 times larger than that of the traditional filtration device. This means that the capability of processing samples in the unit time is greatly improved, and the time for processing samples with the same volume is greatly reduced.

3. Reduction of the pressure on the surface of the filter membrane by three-dimensional filtration: cells are very delicate, and have strong deformability. Thus, in the cell sorting, especially the sorting of the living cells, it is very important to adopt a low pressure filtration to keep the activity of the cells. With the three-dimensional filtration method in which the track-etched membrane wraps the lower end of and the side surfaces all around the bracket of the separation column, the pressure on the membrane of which reduces 9-12 times as compared with the conventional plane-typed filtration method, the integrity of the cell (for example, the red blood cell in the blood of an human body) may be effectively protected.

4. Unnecessary to add the medium: the device physically filters the cells without the addition of chemical substances which may affect the cell activity and the solution property. In this way, after the filtration, forms and activities of the target cells and non-target cells will not be destroyed, and the property of the original solution will not be destroyed.

5. Large amount of samples: the circulation loop of membrane filtration device for fluid of the present disclosure may filter a cell suspension of more than 5000 milliliters (substantially equivalent to the total amount of the blood in the human body) with one operation, and is especially suitable for the filtration of the cell suspension having large amount of samples.

In addition to the purposes, features, and advantages mentioned above, the present disclosure also has other purposes, features and advantages. The present disclosure will be further described in detail below with reference to the drawings.

BRIEF DESCRIPTION OF DRAWINGS

The accompanying drawings which constitute a part of the present application are used to provide further understanding of the present disclosure. Schematic embodiments the present disclosure and the explanations descriptions thereof are used to illustrate the present disclosure and do not constitute improper limitation to the present disclosure. In the accompanying drawings.

REFERENCE NUMERAL

1. first driving pump; 2. second driving pump; 3. separation column; 4. detection column; 5. first three-way valve; 6. second three-way valve; 7. track-etched membrane; 8. liquid channel port; 9. third three-way valve; 10. forth three-way valve; 11. first secondary pump; 12. second secondary pump; 13. fixing brackets; 14. support plate; 15. port cover plate; 16. display screen; 17. conduit line heater; 18. cell liquid container; 19. sub filtration column; 20. sample injection port; 21. sample discharge port; 1*a*. main circulation conduit; 11*b*. conduit connecting the first secondary pump 11 to the main circulation conduit; 12*b*. conduit connecting the second secondary pump 12 to the main circulation conduit; 2*c*. conduit connecting the second driving pump to the main circulation conduit; 2*c*'. conduit connecting the detection column to the main circulation conduit.

DETAILED DESCRIPTION

The embodiments of the present disclosure are illustrated in detail according in combination with the accompanying drawings. However, the present disclosure may be implemented according to a plurality of different methods defined and covered by the claims.

The present disclosure provides a device for separating circulating tumor cells in blood, which comprises a first driving pump communicating with an sample injection port, a separation column, a detection column, a second driving pump for driving cells separated from the separation column to enter the detection column, and several three-way valves as well as secondary driving pumps, wherein, one end of the separation column is connected with the first driving pump through a first three-way valve; the other end is connected with the second driving pump through a second three-way valve; the detection column is connected with a third channel port of the first three-way valve, and a third channel port of the second three-way valve is connected with a sample discharge port; wherein, a cell liquid container (a living animal) is detachably communicated (communicating with the arteries and the veins of the living animal) between the sample injection port and the sample discharge port, so that the cell liquid container together with the device of the present disclosure forms a circulation passage; wherein, the device further comprises a main circulation conduit sequentially communicating the sample injection port, the first driving pump, the first three-way valve, the separation column, the sample discharge port, the cell liquid container, and the sample injection port; wherein, a third three-way valve for adding anticoagulant physiological saline into the main circulation conduit is connected on the main circulation conduit, and is positioned between the sample injection port and the separation column; a fourth three-way valve for adding anticoagulant antagonist into the main circulation conduit is connected on the main circulation conduit, and is positioned between the sample discharge port and the separation column; the separation column includes at least five sub filtration columns in parallel; the sub filtration column comprises a fixing bracket and a track-etched membrane of polycarbonate or polyester material attached to the bottom of and the side surface all around the fixing bracket, the pore diameter of the track-etched membrane being 5-25 μm; wherein, the detection column comprises two portions which are movably connected, the outer sides of the free ends of said two portions are provided with liquid channel ports adapted to the conduit, a sealed hollow cavity is formed between said two portions, and the hollow cavity is provided with one or more layers of the track-etched membranes of polycarbonate or polyester material, the pore diameter of the track-etched membrane being 5-25 μm.

In a case where the first three-way valve 5 rotates to different positions, the separation column 3 may be in communication with any one of the first driving pump and the detection column 4 respectively.

The separation column 3 includes therein at least five sub filtration columns in parallel. The sub filtration column comprises a fixing bracket 13 and a track-etched membrane 7 attached to the bottom of and the side surfaces the fixing bracket, and sorting of cells in a three-dimensional wrapping way without dead angle has a better efficiency. When the cell suspension flows through the separation column 3, cells with a size larger than 5-25 μm will be intercepted and held up inside the sub separation column by the track-etched membrane 7, and small cells may pass through freely. The pore diameter of the track-etched membrane 7 is preferably 8-10 μm.

The track-etched membrane 7 may be made of polycarbonate or polyester, neither of which affects the implementation of the present embodiment. The track-etched membrane adopts the isotope track-etched technique, which leads to a smooth membrane surface, evenly distributed pores, and highly consistent and smooth pore diameters, and thus the membrane is an idea material for separating the biological cells. The track-etched membrane sold in prior arts may be used as the track-etched membrane 7 described in the present disclosure.

Figure 3:
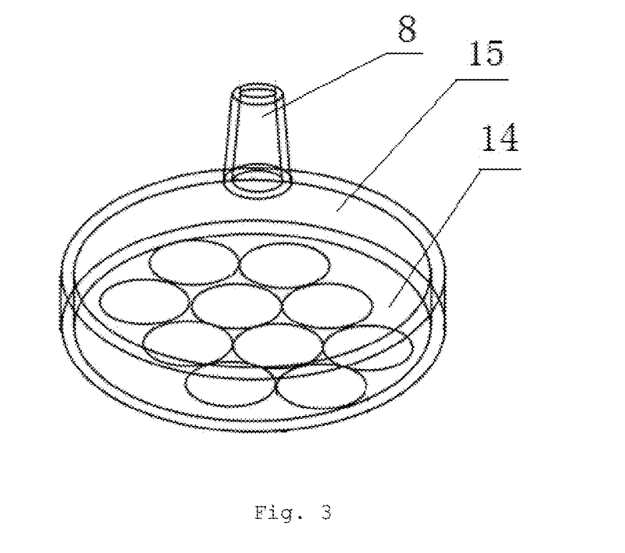
FIG. 3 is a schematic drawing showing the structure of one end of the separation column of the preferable embodiment of the present disclosure.
Figure 4:
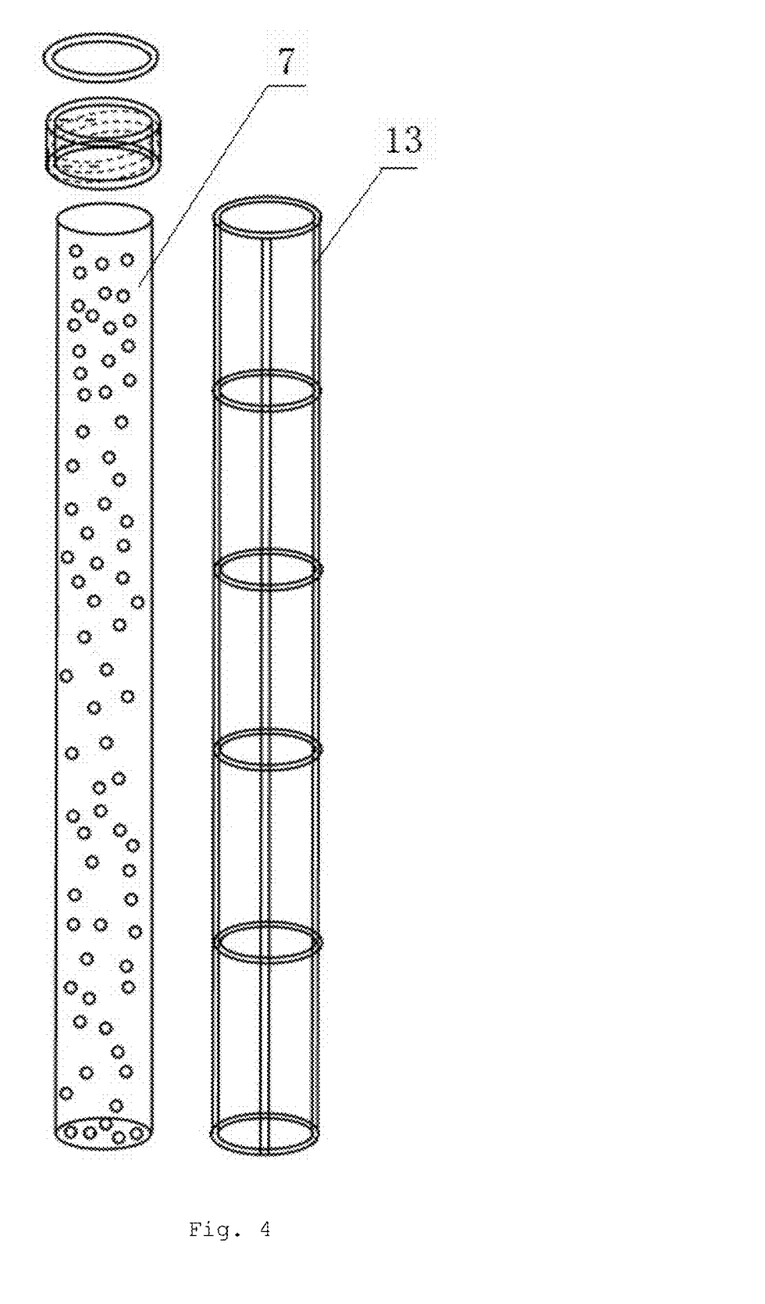
FIG. 4 is schematic drawing showing the structure of the separation column of the preferable embodiment of the present disclosure.
Figure 5:
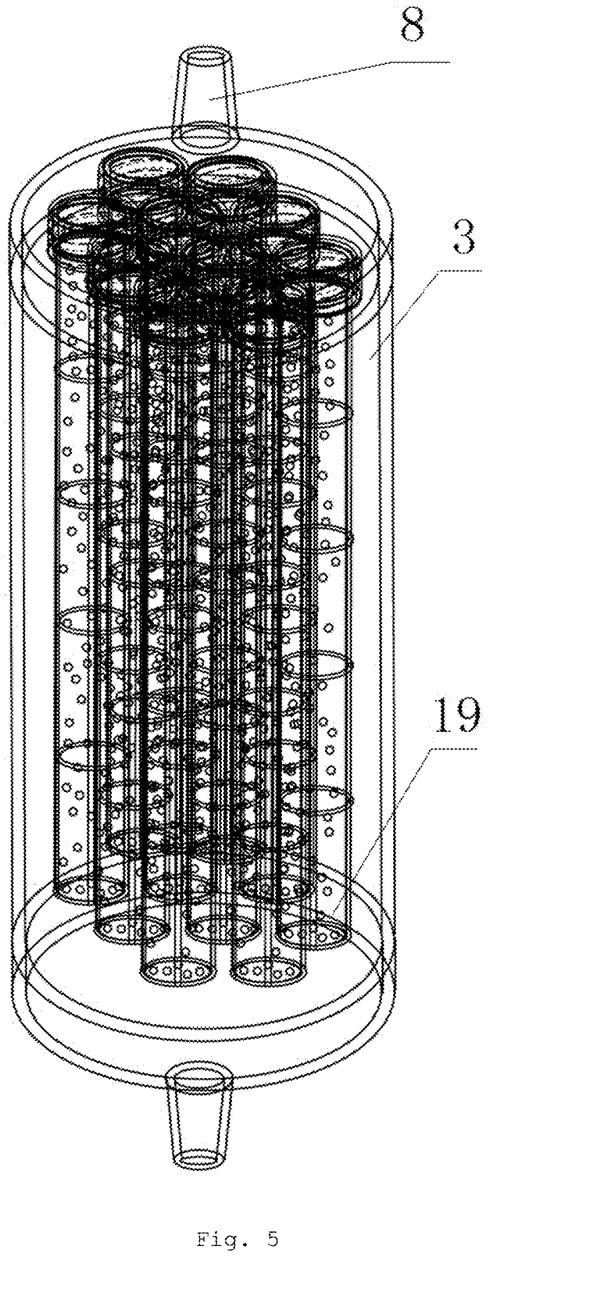
FIG. 5 is a schematic drawing showing the overall structure of the separation column of the preferable embodiment of the present disclosure.

As seen from FIG. 3, FIG. 4 and FIG. 5, the separation column may further comprises port cover plates 15 of two ends, a support plate 14 within the port cover plates 15 and sub filtration columns, wherein the sub filtration columns are positioned between the support plate 14 of the sample injection port and the port cover plate 15 of the sample discharge port (the end close to the sample discharge port may be either provided with a support plate or without a support plate), and are constituted by several fixing brackets and the track-etched membrane. Each of the above means may be disassembled and used flexibly. It is also possible that different numbers of the sub filtration columns 19 may be provided according to different requirements. Several round holes may be provided on the support plate 14 and are configured to jam the fixing bracket 13 so as to stabilize its structure. The port cover plate 15 is provided with the liquid channel port 8 adapted to the conduit to facilitate the suspension flowing through. FIG. 4 and FIG. 5 show that, in each sub filtration column, the track-etched membrane 7 is connected thereabove with a sealing ring and a threaded coupling, the purpose of which is to form a good seal between the support plate 14 and the sub filtration column 19.

When the cylindrical sub filtration column has a bottom surface diameter of 8 mm and a length of 10 cm, 10 sub filtration columns are in parallel with the exterior sealed and surrounded by a housing of polycarbonate material, and the total filtration area of the filtration column is 256 $cm^2$. Such design may increase the filtration area on one hand, and may enable the filter membrane to bear larger pressure on the other hand.

Figure 6:
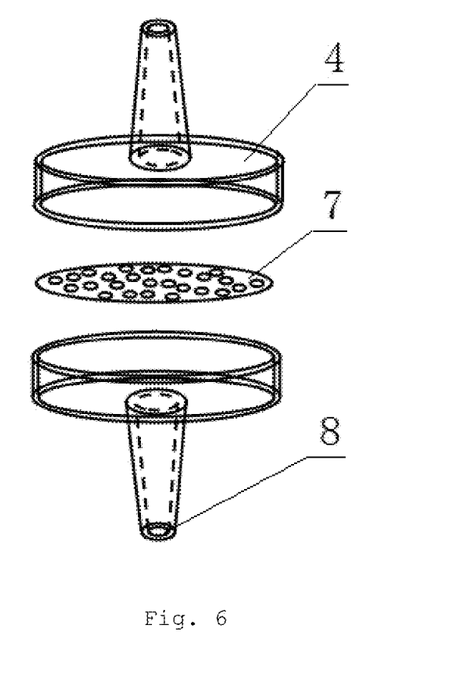
FIG. 6 is a schematic drawing showing the break-down structure of the detection column of the preferable embodiment of the present disclosure.

As seen from FIG. 6, the detection column 4 may be made of plasticized polyvinyl chloride, and comprises an upper portion and a lower portion which are movably connected. Liquid channel ports 8 adapted to the conduit are both provided at the outer sides of said two portions. The hollow cavity between the sealed two portions is provided with a layer of the track-etched membrane 7 where the pore diameter of the track-etched membrane is 5-25 μm, preferably 8-10 μm. When the cell suspension flows through the detection column 4 via the liquid channel port 8, cells with a size larger than 5-25 μm will be intercepted and held up by the track-etched membrane 7.

Figure 1:
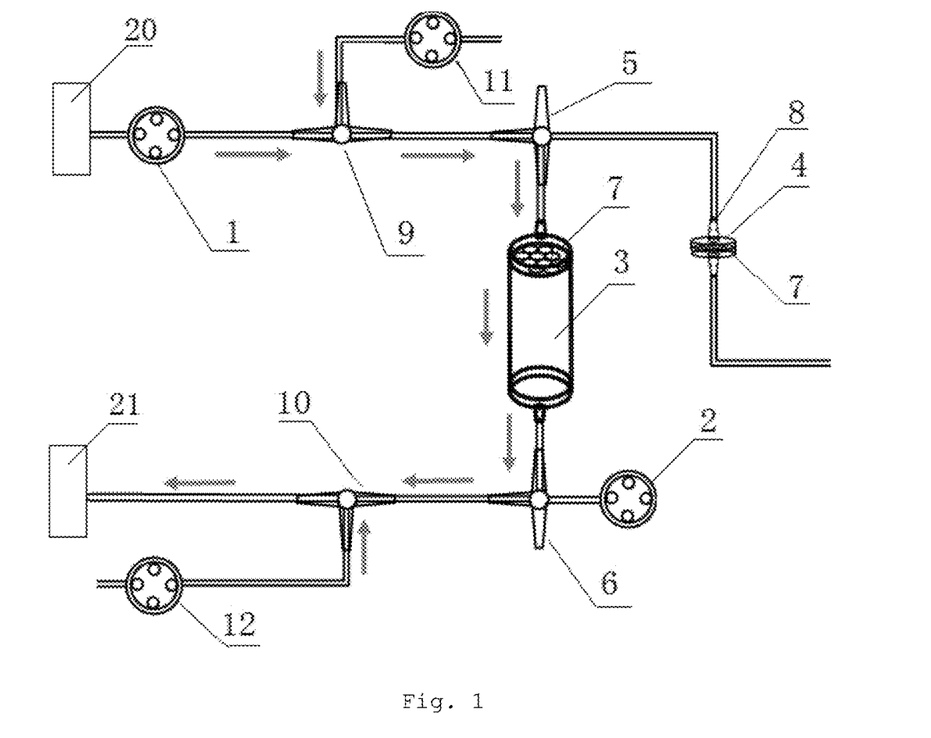
FIG. 1 is a schematic drawing showing the structure of the separation passage of a preferable embodiment of the present disclosure (the direction of the arrows in FIG. 1 is the flowing direction of the fluid)
Figure 2:
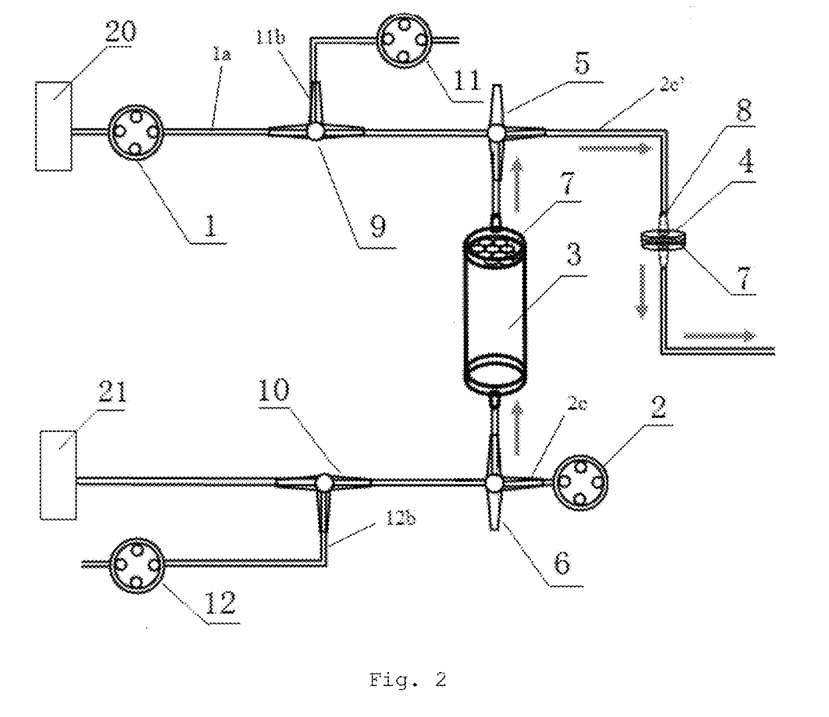
FIG. 2 is a schematic drawing showing the structure of the detection passage of the preferable embodiment of the present disclosure (the direction of the arrows in FIG. 1 is the flowing direction of the fluid)

As seen from FIG. 1 and FIG. 2, the device of the present disclosure forms two operation passages by using the three-way valves, the separation column and the detection column. The first passage is as shown in FIG. 1 (in FIG. 1, the direction of the arrows indicates the flowing direction of the fluid), and cell suspension with large amount of samples enters the separation column 3 from the cell liquid container 18 through the sample injection port 20, the first driving pump 1, and the first three-way valve 5, and discharges from the other end, then flows back to the cell liquid container 18 through the sample discharge port 21 after being filtered, which achieves the purpose of separating particular cells with large volumes effectively. Because the separation is performed through a uninterrupted circulation, namely, the cell liquid container-the pump-the separation column, it may be guaranteed that the total volume of the cell suspension outside the membrane filtration system for fluid remains unchanged during the separation process, wherein the number of the cells of small volumes remains unchanged. FIG. 1 further includes injecting anticoagulant physiological saline to the main circulation conduit from the conduit 11*b* and injecting anticoagulant antagonist to the main circulation conduit from the conduit 12*b*.

For example, when the living animal (including human) is taken as the specific cell liquid container, the blood may be led out from the artery through a pump, and then transfused into the vein after being filtered by the separation column, leading to the separation of the particular cells with no influence on the health of the living animal.

The second passage is as shown in FIG. 2 in which the three-way valve is adjusted, the connection channel of the sample injection port 20 and the separation column 3 is closed, the fluid (for example, the physiological saline) flows through the separation column 3 from the second driving pump 2 reversely (flows in a direction opposite to the flowing direction of the fluid in the main circulation conduit), and discharges from the other end, and then enters the detection column 4. This passage further enriches the particular cells with large volumes retained from the separation column 3 (firstly the cells with large volumes are made detached from the membrane in the separation column 3 under the effect of the second driving pump 2, then the physiological saline containing those cells with large volumes enters the detection column 4), concentrates the cells on the filter membrane (the track-etched membrane) of the detection column 4 which facilitates performing downstream operation and detection on the cells on the membrane. The wasted liquid discharges from the other end of the detection column 4.

The device of the present disclosure completes substantially at least the following three steps. Step A is circulation and filtration where target cells in a first flow of fluid (for example, the blood) are retained by the track-etched membrane in the separation column under the circulation and filtration condition. Step B is detachment where a second flow of fluid (for example, the physiological saline) flows in a direction opposite to that of the first flow of fluid so that the target cells originally retained are detached from the membrane. Step C is reception or enrichment of the cells where the cell reception means to use a container to completely receive the target cells and the second flow of fluid and the cell enrichment means to filter the second flow of fluid by using the detection column 4 having the track-etched membrane and simultaneously enrich the target cells on the upstream side of the track-etched membrane. Apparently, in step C, the enrichment method provided in the present disclosure is more preferable. In this way, it is unnecessary to perform further cell enrichment on the received solution by using the conventional method such as a centrifuge. In addition, a washing step may be comprised before and after "step A of circulation and filtration" described above in the present disclosure. Specifically, the physiological saline is used to wash the conduits in the device. The washing step after the step of circulation and filtration may cause the blood from the body of the cell liquid container 18 to flow back into the body of the cell liquid container 18 completely without any blood remaining in the conduit line device.

Figure 7:
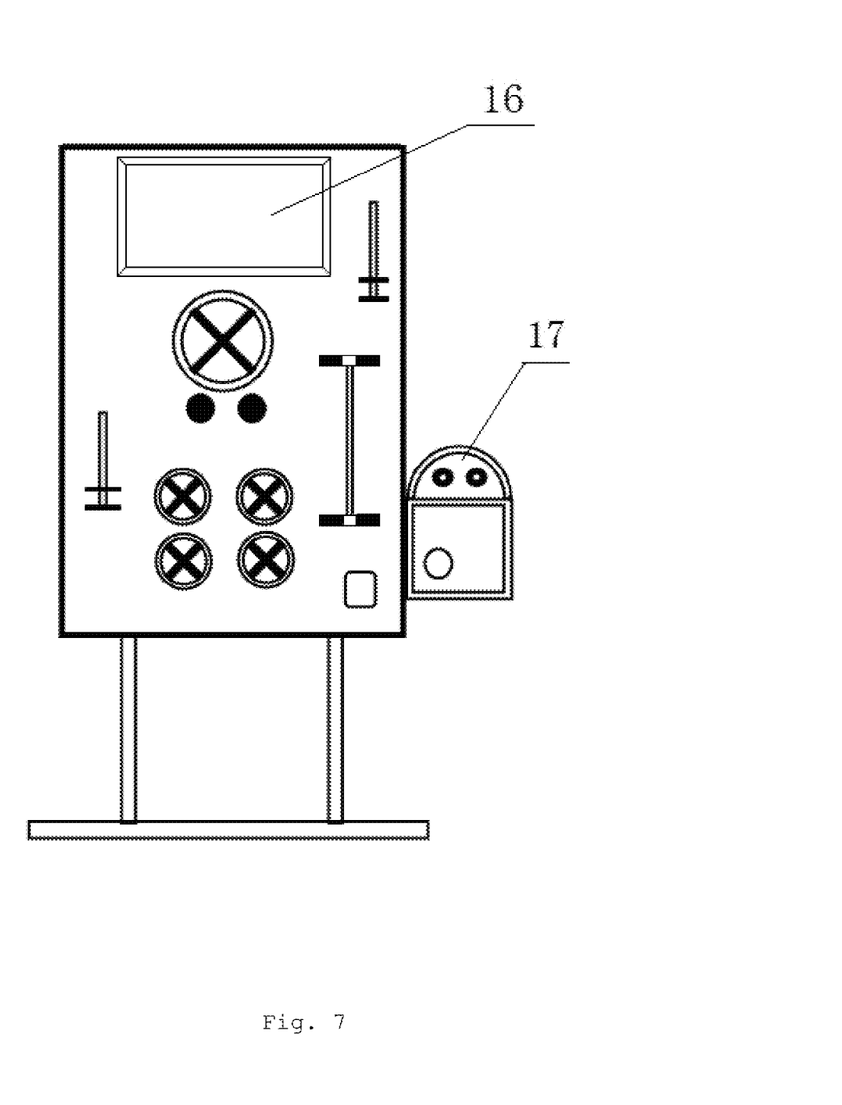
FIG. 7 is a schematic drawing showing the appearance structure of the preferable embodiment of the present disclosure.

As seen from FIG. 7, the device of the present disclosure is an integrated machine composed of components, such as a touch display screen 16, a primary peristaltic pump, a pressure sensor, a secondary peristaltic pump, a push-type infusion pump, filtration column fixing brackets, an air discharge device, a conduit line heater and a base bracket, and connecting conduits, and the device has the characteristics of compact structure, comprehensive function, and timely information sampling. In the device, the touch display screen 16 which is a terminal displaying operation situation of each component is connected with a main board of the machine and displays key information such as pressure, flow rate, rotation speed, temperature and time with a hand touch function enabling control of operations of other components on the screen. The primary peristaltic pump, which is a main device for providing power, provides power by causing the steel column in the rotary disk to contact the conduit wall and extruding the conduit wall. The pressure sensor is configured to detect the pressure variation in the conduit line and detect whether the whole system is running smoothly. The push-type infusion pump may continuously provide the conduits with medicines (anticoagulant physiological saline or anticoagulant antagonist) necessary for guaranteeing the smooth flow of the fluid without generation of solid impurity. The filtration column fixing bracket is used to fix the membrane filtration column. The air discharge device may discharge the air in the conduit line and prevent the air from entering the connecting conduits. The conduit line heater 17 may heat the fluid in the conduit line so as to maintain the fluid at the most appropriate survival temperature for cells of 37° C. The conduit line heater 17 may be connected with any part of the conduits, for example, the sample injection port, the first three-way valve, the second three-way valve, the cell liquid container, and the sample discharge port.

Figure 9:
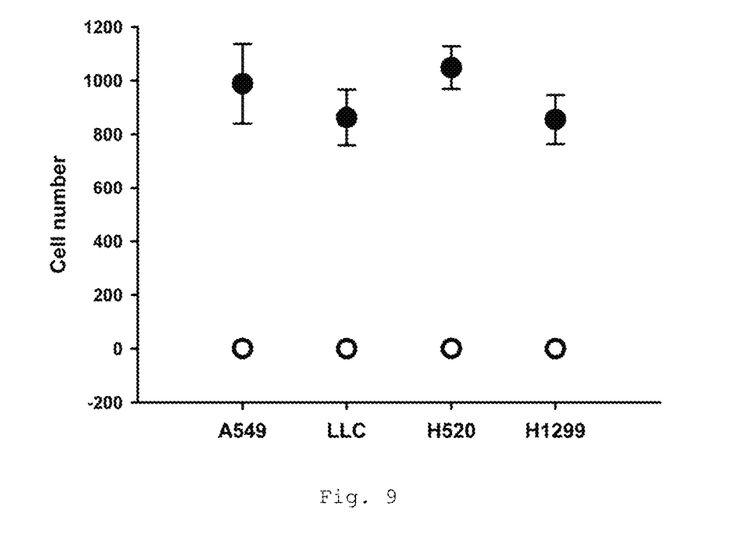
FIG. 9 is a diagram showing the data comparison between the experiment results in the preferable embodiment of the present disclosure and a conventional device.

As seen from FIG. 9, the separation results of the vitro experiments performed by the device of the present disclosure and conventional separation device are compared.

Firstly, preparing which is formed by four types of lung cancer cells, namely, A549, LLC, H520, H1299, the quantity of each of which is 1000, forms 5 L of cell suspension together with the physiological saline.

The separation column in the device of the present disclosure has a diameter of 6 cm and a length of 11 cm, and contains 11 cylindrical sub filtration columns in parallel, each of which has a diameter of 1 cm and a length of 10 cm. The total effective filtration area of the separation columns is 354 square centimeters. The cell suspension flows in a circulation manner on the separation column. The total volume of the cell suspension processed by the separation column is 5 L, and the fluid flowing velocity is 250 milliliter per minute.

As for the conventional separation device, the separation column thereof has a shape and a structure similar to those of the detection column 4 in the present disclosure, and the track-etched membrane thereof with pore diameter of 6 centimeter has an effective filtration area of 28.26 square centimeters. The cell suspension is filtered on the separation column once, rather than flow in a circulation manner, and the total volume of the cell suspension processed by the separation column is 5 ml. Thus, theoretically, the cell suspension contains approximately only one cell.

In FIG. 9, the solid dots indicate results obtained by the device of the present disclosure, and the hollow dots indicate results obtained by the conventional separation device. As can be seen from the drawing, the number of complete undamaged lung cancer cells of four types, namely, A549, LLC, H520, H1299 sorted by the device of the present disclosure are 988.33±148.17, 862.67±103.65, 1048±79.3, 855±91.39, respectively. The 1000 cells configured to be used in the cell suspension and the result data in FIG. 9 are all obtained by the cell counter, and thus there might be some errors. A plurality of separation results of the conventional separation device may fluctuate around the theoretical value (1 tumor cell), and thus the resultant data cannot be used to accurately determine whether there are circulating tumor cells in the blood of the living animal (including human body) or how many circulating tumor cells there are in the blood.

The tumor cell has a size larger than that of the normal blood cell. In the device of the present disclosure, during the process when the blood flows through the separation column once, a portion of tumor cells may possibly pass through the membrane, and an extremely small portion of blood cells may be retained on the membrane. However, because the separation steps of the device in the present disclosure are performed in a circulation manner, after the blood flows through the separation column several times, the normal blood cells and tumor cells can be separated by the membrane thoroughly.

One skilled in the art may easily understand that the technical solution of the claims (especially claim 1) of the present disclosure may be replaced by the equivalents in the following aspects.

First, the three-way valves may be equivalently replaced by a three-way conduit plus cut-off valves (e.g., shutoff valves, ball valves, butterfly valves, gate valves, etc.) respectively provided on the conduit.

Figure 10:
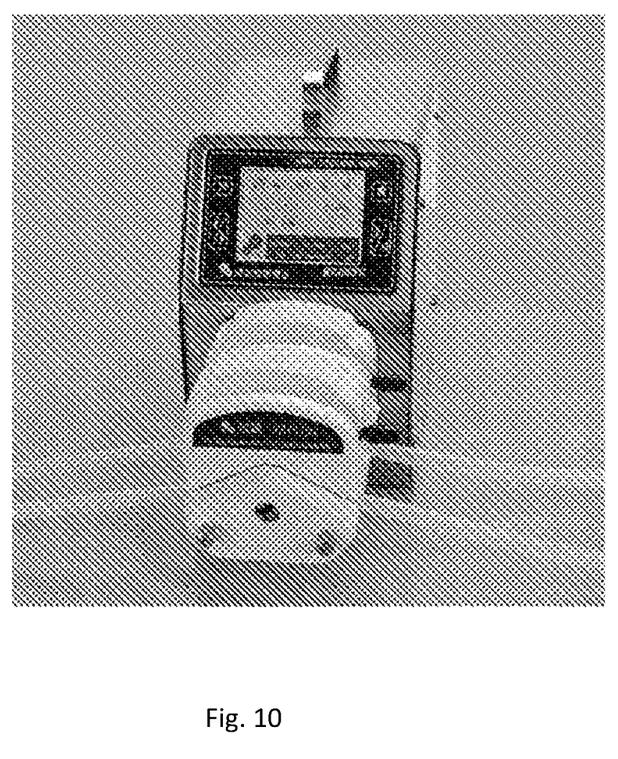
FIG. 10 is a schematic drawing showing the structure of the pump heads of the peristaltic pump in parallel connection in the prior arts or the present disclosure.

Second, a plurality of peristaltic pumps may be equivalently replaced by a peristaltic pump plus a plurality of parallel conduits provided thereon (the picture of the peristaltic pump provided in FIG. 10 shows a case where a peristaltic pump is equipped with a plurality of pump heads in parallel). For example, both the conduit 11b (the conduit connecting the first secondary pump 11 to the main circulation conduit) and the conduit 12b (the conduit connecting the second secondary pump 12 to the main circulation conduit) may be independently connected on the first driving pump, and be parallel with the main circulation conduit 1a connected on the first driving pump 1. Thus, by using only one peristaltic pump (namely, the first driving pump 1), the functions of the three peristaltic pumps 1, 11, and 12 in the present disclosure may be replaced and achieved. A plurality of parallel connections may also be applied, for example, the first secondary pump 11 being connected in parallel with the second secondary pump 12, the first driving pump 1 being connected in parallel with the first secondary pump 11 and the like. For example, when the device of the present disclosure is provided with three pump heads of the peristaltic pump in total (another pump is the push pump), either two of the three pump heads may be in parallel while the rest is independent, or the three pump heads are in parallel.

Third, FIG. 1 and claim 1 of the present disclosure defines that the fluid flows according to the following order: from the sample injection port 20, to the first driving pump 1, the first three-way valve and the separation column 3. However, by reading the present disclosure, one skilled in the art may know that it is sufficient as long as the detection column 4 is connected to the upstream end of the separation column 3 in the fluid flowing direction in the main circulation conduit (rather than connected to the downstream end of the separation column 3). Thus, position exchange between the first driving pump 1 and the first three-way valve 5 is an alternative equivalent of the present disclosure. That is, in the main circulation conduit, the fluid flows in the following order: from the sample injection port 20 to the first three-way valve 5, the first driving pump 1 and the separation column 3.

Fourth, the second driving pump 2 and the detection column 4 of the present disclosure respectively serve the function of detachment (which causes the cells retained on the membrane in the separation column 3 to be detached from the membrane) and enrichment (which causes the target cells to be enriched on the membrane of the detection column) effects, respectively. In fact, the detection column 4 may be replaced by an equivalent of a receiving container plus centrifugal separation steps. That is to say, in the present disclosure, it is possible to connect a receiving container (e.g. a volumetric flask, a beaker) instead at the position of the detection column 4, and transfer the fluid in the receiving container at one or more times into the centrifugal conduit to be centrifuged and enriched so as to obtain target cells, and then deliver the enriched target cells to be counted under the detection apparatus.

Moreover, although claim 1 of the present disclosure defines that the number of the sub filtration columns 19 in the separation column is five or more in parallel, one skilled in the art may arrange 4, 3, 2, or even 1 sub filtration column(s). Even if provided with only one sub filtration column, the separation column has better filtration effect as compared with the case where the device of the present disclosure is connected to a separation column (the structure of which is similar to the detection column 4 in the present disclosure) having only one layer of round planar membrane. Such technical solution in which the number of the sub filtration columns is less than five also belongs to the alternative equivalents of the present disclosure (for example, through a conventional design of the shape and size of the membrane conduit, the difference of 4 sub filtration columns from 5 sub filtration columns can be compensated).

In addition, although claim 1 of the present disclosure defines the track-etched membrane of polycarbonate or polyester material at the bottom and the side surface of the fixing bracket of the sub filtration column, when the surface area of the bottom of the fixing bracket of the sub filtration column is far less than (for example, the sum of the surface areas of the side surfaces is 5 times or more as large as the surface area of the bottom) the surface areas of the side surfaces all around, it is possible to provide no track-etched membrane on the bottom surface (basically the surface area of the bottom may be ignored with respect to the total surface area), and instead adopt other materials (for example, plasticized polyvinyl chloride) to perform sealing. Alternatively, the total area of one surface of the fixing bracket is extremely small, and thus the prior art cannot provide the track-etched membrane on the surface. At this time, it is possible to provide no membrane on the bottom surface or one or more side surfaces all around, and instead adopt other materials to perform sealing. Such a method also belongs to the alternative equivalents of the technical solution of claim 1 of the present disclosure. The above are merely preferable embodiments of the present disclosure and are not intended to limit the present disclosure. For one skilled in the art, various modifications and changes may be applied to the present disclosure. All modifications, equivalents, improvements made within the spirit and principle of the present disclosure should be included in the protection scope of the present disclosure.

The invention claimed is:

1. A device for separating cells in fluid, comprising a first driving pump communicating with an sample injection port, a separation column, a detection column, a second driving pump for driving cells separated from the separation column to enter the detection column, and several three-way valves as well as secondary driving pumps, wherein one end of the separation column is connected with the first driving pump through a first three-way valve, the other end of the separation column is connected with the second driving pump through a second three-way valve, the detection column is connected with a third channel port of the first three-way valve, and a third channel port of the second three-way valve is connected with a sample discharge port, when a cell liquid container is detachably connected between the sample injection port and the sample discharge port, the cell liquid container together with the device forms a circulation passage, the device further comprises a main circulation conduit sequentially communicating with the sample injection port, the first driving pump, the first three-way valve, the separation column, the sample discharge port, the cell liquid container, and the sample injection port, a third three-way valve for adding anticoagulant physiological saline into the main circulation conduit is connected on the main circulation conduit, and is positioned between the sample injection port and the separation column, a fourth three-way valve for adding anticoagulant antagonist into the main circulation conduit is connected on the main circulation conduit, and is positioned between the sample discharge port and the separation column, the separation column includes at least five sub filtration columns connected in parallel, the sub filtration column comprises a fixing bracket and a track-etched membrane of polycarbonate or polyester material attached to a bottom of and a side surface all around the fixing bracket, and a pore diameter of the track-etched membrane is 5-25 μm, and the detection column comprises two portions which are movably connected, outer sides of free ends of said two portions are both provided with liquid channel ports adapted to the conduit, a sealed hollow cavity is formed between said two portions, one or more layers of track-etched membranes of polycarbonate or polyester material are provided in the hollow cavity, and a pore diameter of the track-etched membrane is 5-25 μm.

2. The device according to claim 1, wherein a first secondary pump is connected to a third channel port of the third three-way valve, and a second secondary pump is connected to a third channel port of the forth three-way valve.

3. The device according to claim 1, wherein the third three-way valve is positioned between the sample injection port and the first driving pump, or the third three-way valve is positioned between the first driving pump and the separation column, and the forth three-way valve is positioned between the sample discharge port and the second three-way valve, or the forth three-way valve is positioned between the second three-way valve and the separation column.

4. The device according to claim 1, wherein the pore diameter of the track-etched membrane in the detection column is smaller than or equal to the pore diameter of the track-etched membrane in the separation column.

5. The device according to claim 1, wherein the separation column comprises a liquid dispersion region positioned at one end of the separation column close to the sample injection port and sub filtration columns positioned in a mid-section of the separation column.

6. The device according to claim 5, wherein one end surface of the liquid dispersion region is a port cover plate with a liquid channel port opened thereon, and the other end surface of the liquid dispersion region is a support plate with through holes opened therein corresponding to a total number of end surfaces of the sub filtration columns.

7. The device according to claim 1, wherein the driving pump is a peristaltic pump.

8. The device according to claim 2, wherein the first secondary pump or the second secondary pump is a peristaltic pump or a push-type infusion pump.

9. The device according to claim 1, wherein the device further comprises a pressure sensor, which is provided on the main circulation conduit, and is positioned between the first driving pump and the separation column, and the device further comprises a conduit line heater.

10. The device according to claim 1, wherein the pore diameters of the track-etched membranes in the separation column and the detection column are both 8-10 μm.

11. The device according to claim 1, wherein the detection column is made of plasticized polyvinyl chloride.

* * * * *